(12) United States Patent
Anderson et al.

(10) Patent No.: US 11,318,467 B2
(45) Date of Patent: May 3, 2022

(54) ASSAY STRUCTURES FOR MULTI-STEP BIOCHEMICAL ASSAYS

(71) Applicant: Tokitae LLC, Bellevue, WA (US)

(72) Inventors: Caitlin E. Anderson, Seattle, WA (US); Joshua Davis Bishop, Seattle, WA (US); David Michael Cate, Bellevue, WA (US); Benjamin David Grant, Bellevue, WA (US); Toan Huynh, Seattle, WA (US); Damian Madan, Issaquah, WA (US); Kevin Paul Flood Nichols, Issaquah, WA (US); Bernhard Hans Weigl, Seattle, WA (US)

(73) Assignee: Tokitae LLC, Bellevue, WA (US)

( * ) Notice: Subject to any disclaimer, the term of this patent is extended or adjusted under 35 U.S.C. 154(b) by 230 days.

(21) Appl. No.: 16/886,934

(22) Filed: May 29, 2020

(65) Prior Publication Data

US 2021/0370290 A1  Dec. 2, 2021

(51) Int. Cl.
*B01L 3/00* (2006.01)
*C12M 1/00* (2006.01)
*C12M 1/12* (2006.01)

(52) U.S. Cl.
CPC ......... *B01L 3/50273* (2013.01); *C12M 23/28* (2013.01); *C12M 25/14* (2013.01); *B01L 2200/025* (2013.01); *B01L 2300/0681* (2013.01); *B01L 2300/0816* (2013.01); *B01L 2300/0874* (2013.01); *B01L 2400/0406* (2013.01); *B01L 2400/0683* (2013.01)

(58) Field of Classification Search
None
See application file for complete search history.

(56) References Cited

U.S. PATENT DOCUMENTS

| | | | |
|---|---|---|---|
| 4,999,285 A | 3/1991 | Stiso | |
| 7,189,522 B2 | 3/2007 | Esfandiari | |
| 8,507,259 B2 | 8/2013 | Esfandiari | |
| 8,628,729 B2 | 1/2014 | Carrilho et al. | |
| 9,068,981 B2 | 6/2015 | Babu et al. | |
| 2010/0239458 A1 | 9/2010 | Mink et al. | |
| 2011/0319279 A1* | 12/2011 | Montagu | B01L 3/502746 506/18 |
| 2014/0093980 A1 | 4/2014 | Fu et al. | |

(Continued)

FOREIGN PATENT DOCUMENTS

CN 208715838 U 4/2019

OTHER PUBLICATIONS

Elif Burcu Bahadir et al.; "Lateral flow assays: Principles, designs and labels"; Trends in Analytical Chemistry; 2016; pp. 286-306; vol. 82; Elsevier B.V.

(Continued)

*Primary Examiner* — Matthew D Krcha
(74) *Attorney, Agent, or Firm* — Adam L. K. Philipp; Shan Liao; AEON Law

(57) ABSTRACT

Embodiments include assay devices within a single use, disposable cassette for biochemical assays with at least one fluid well and at least one capillary valve. The capillary valve in combination with motion of porous sheets within the assay leads to addition of liquid reagents at different times to the assay although a user adds the liquid reagents to the cassette simultaneously.

32 Claims, 18 Drawing Sheets

(56) References Cited

U.S. PATENT DOCUMENTS

2015/0098873 A1* 4/2015 Ku ............................ B01L 3/545
422/403
2019/0134637 A1 5/2019 Bishop et al.

OTHER PUBLICATIONS

Hansang Cho et al.; "How the capillary burst microvalve works"; Journal of Colloid and Interface Science; 2007; pp. 379-385; vol. 306; Elsevier Inc.
"Critical Surface Tension and Contact Angle with Water for Various Polymers;" located at https://www.accudynetest.com/polytable_03.html?rd=self&sortby=contact_angle; 2020 and printed on May 19, 2020; pp. 1-5; Diversified Enterprises.
"DPP® (Dual Path Platform) Technology MS-12-015 Rev 4 Licensing Opportunities: Ideal for Multiplexing Antigen and/or Antibody Detection"; located at http://chembio.com/wp-content/uploads/2014/11/DPP-Technology-Sheet.pdf; p. 1; CHEMBIO Diagnostic Systems, Inc.
Katarzyna Szymczyk et al.; "Effect of Polysorbates on Solids Wettability and Their Adsorption Properties"; Colloids and Interfaces; 2018; pp. 1-15; vol. 2, issue 26; Multidisciplinary Digital Publishing Institute.
Bhushan J. Toley et al.; "A versatile valving toolkit for automating fluidic operations in paper microfluidic devices"; Lab Chip; Mar. 21, 2015; pp. 1432-1444; vol. 15, No. 6; Department of Health and Human Services, USA.
Tobias Broger et al.; "Novel lipoarabinomannan point-of-care tuberculosis test for people with HIV: a diagnostic accuracy study"; Lancet infect Dis; Aug. 2019; pp. 852-861; vol. 19; Elsevier Ltd.
Joshua Ronald Buser; "Heat, Fluid, and Sample Control in Point-of-Care Diagnostics"; A dissertation submitted in partial fulfillment of the requirements for the degree of Doctor of Philosophy, University of Washington; 2016; pp. 1-463.
Elain Fu et al.; "Progress in the development and integration of fluid flow control tools in paper microfluidics"; Lab Chip; Jan. 13, 2017; pp. 614-628; vol. 17; The Royal Society of Chemistry.
Hao Fu et al.; "A paper-based microfluidic platform with shapememory-polymer-actuated fluid valves for automated multi-step immunoassays"; Microsystems & Nanoengineering; 2019; pp. 1-12; vol. 5, No. 50; Nature.
Allison Golden et al.; "Extended Result Reading Window in Lateral Flow Tests Detecting Exposure to Onchocerca volvulus: A New Technology to Improve Epidemiological Surveillance Tools"; Plos One; Jul. 2013; pp. 1-9; vol. 8, Issue 7; Plos One.
Gyeo-Re Han et al.; "An Automated, Universal, and Mass-Producible Paper-Based Lateral Flow Biosensing Platform for High-Performance Point-of-Care Testing"; ACS Applied Materials & Interfaces; Dec. 9, 2019; pp. 1-12; American Chemical Society.
Katarzyna M. Koczula et al.; "Lateral flow assays"; Essays in Biochemistry; Jun. 30, 2016; pp. 111-120; vol. 60; Portland Press Limited.
Mikinaga Mori et al.; "Development of Highly Sensitive Immunochromatographic Detection Kit for Seasonal Influenza Virus Using Silver Amplification"; Fujifilm Research & Development; Feb. 27, 2012; pp. 5-11; Fujifilm Corporation.
Sunanda Roy et al.; "High Performance of Cyclic Olefin Copolymer-Based Capillary Electrophoretic Chips"; ACS Applied Materials & Interfaces; Jun. 10, 2013; pp. 5683-5689; vol. 5; American Chemical Society.
Diana Rymuszka et al.; "Wettability and thermal analysis of hydrophobic poly(methyl methacrylate)/silica nanocomposites"; Adsorption Science & Technology; Feb. 28, 2017; pp. 560-571; vol. 35, Nos. 5-6; Sage.
Jun Hui Soh et al.; "Strategies for developing sensitive and specific nanoparticle-based lateral flow assays as point-of-care diagnostic device"; Nano Today; Jan. 3, 2020; pp. 1-17; vol. 30; Elsevier Ltd.
Bhushan J. Toley et al.; "A Powerless Valving System for Fluid Flow in Paper Networks"; 16th International Conference on Miniaturized Systems for Chemistry and Life Sciences, Okinawa, Japan; Oct. 28-Nov. 1,2012; pp. 305-307
PCT International Search Report and Written Opinion; International Patent Application No. PCT/US2021/034276; dated Oct. 6, 2021, 8 pages.

* cited by examiner

ASSAY STRUCTURES FOR MULTI-STEP BIOCHEMICAL ASSAYS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

An assay device includes a cassette and a set of assay components within the cassette. The assay components and cassette are positioned for functional interaction during implementation of the assay. In some embodiments, the assay components are positioned linearly as compatible with reel to reel manufacturing techniques.

In some embodiments, the cassette includes an upper component with a fluid well, a capillary valve, a top section of a mechanical stop region, a top section of a mechanical compression region, and a visualization aperture, as well as a lower component with a bottom portion of the mechanical stop region and a bottom portion of the mechanical compression region. In some embodiments, the cassette includes a second fluid well including an aperture positioned adjacent to a top surface of the first end of the porous sheet within the cassette.

In some embodiments, the set of assay components within the cassette include a porous sheet with a first end and a second end, a wicking material in contact with the second end of the porous sheet, and a compressed material of a size, shape and position to expand sufficiently when wet to move a top surface of the porous sheet adjacent to an aperture of the capillary valve. In some embodiments, the set of assay components within the cassette include a first porous sheet with a first end and a second end, a second porous sheet with a first end and a second end, wherein the second end of the first porous sheet is in contact with the first end of the second porous sheet, a wicking material in contact with the second end of the second porous sheet, and a compressed material of a size, shape and position to expand sufficiently when wet to move a top surface of the porous sheet adjacent to an aperture of the capillary valve. In some embodiments, the set of assay components within the cassette include a first porous sheet with a first end and a second end, a second porous sheet with a first end and a second end, a third porous sheet with a first end and a second end, wherein the second porous sheet overlays the second end of the first porous sheet and the first end of the third porous sheet, a wicking material in contact with the second end of the third porous sheet, and a compressed material of a size, shape and position to expand sufficiently when wet to move a top surface of the second porous sheet adjacent to an aperture of the capillary valve.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
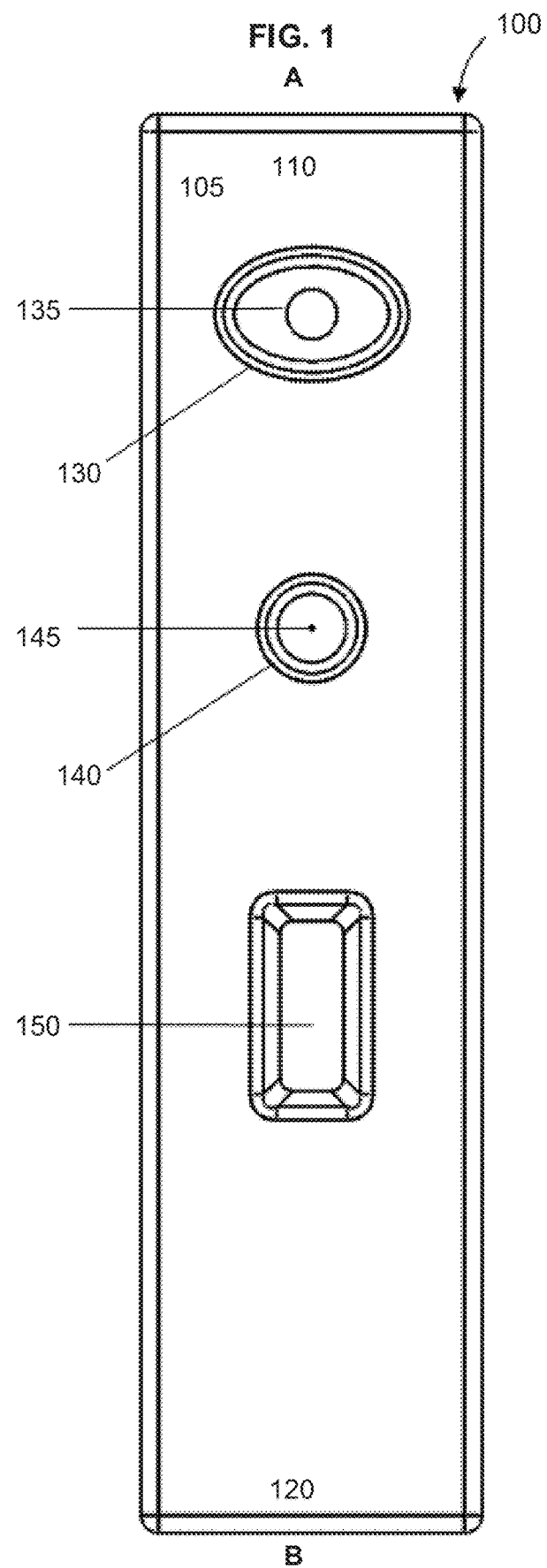
FIG. 1 is an external view of the top cassette face of an assay device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Technologies described herein relate to single-use biochemical assays for diagnostic or screening detection of one or more analytes in a liquid sample. This type of technology includes assays referred to as lateral flow tests, or lateral flow assays ("LFA"). In some embodiments, the assays are lateral flow immunochromatographic assays. These assays are generally designed to provide diagnostic or screening information in a simple, portable format with minimal manipulation by a user. One advantage of the format is a simple to operate, portable test with disposable components that can often be implemented by a person with minimal training or instruction. Generally these assays require addition of a liquid sample to a dry assay structure, and some assays further include addition of a buffer or solvent fluid to the assay. However, assays that require minimal steps or manipulation by a user are preferred for their general applicability and robustness. Minimal intervention from a user can be particularly important in assays intended for use in high-throughput situations where users have little time per assay, as well as in situations where users are not expected to be knowledgeable or experienced in assay steps or procedure. In some embodiments, assay devices are designed for use in low-resource settings.

Assays described herein are designed to improve on existing assay technologies by incorporating features into the assay to permit staged addition of reagents to an assay with minimal additional manipulation and/or steps required by a user. In particular, the structures described herein provide for the addition of multiple fluids, buffers and/or liquid reagents to an assay at a predetermined time after the start of the assay without requiring a user to wait or time the addition of the multiple fluids, buffers and/or reagents. Depending on the embodiment, assays can be calibrated to different times and conditions due to components such as types of materials selected, thickness of materials, and relative position of materials to each other and within the assay. Assays described herein are also envisioned to be compatible with a reel to reel manufacturing system, with the associated low costs and fabrication efficiencies.

Assay types that can be implemented with embodiments of the assay devices described herein include biochemical assays, enzymatic assays, redox chemistry reaction-based assays, and assays including nucleic acid amplification. The specific assay embodiment will include requirements for the timing delay in the steps or stages of the assay as can be implemented by features described herein. The timing delay requirements are dependent on the assay embodiment but are anticipated to vary in length between five minutes and one hour. A first step or stage of an assay can be implemented with addition of a first buffer to a buffer well, and a reagent fluid can be delayed from addition to the assay structure within a capillary valve without further manipulation by a user for a time between five minutes and one hour depending on the structure of the implemented assay device. Different time delays between steps or stages of an assay can be achieved with modifications to an assay device including: gap size between a lower aperture of a capillary valve and a nearby surface of a porous material; length of a wicking material; fluid dispersal properties of the wicking material(s); length of the porous material(s); fluid dispersal properties of the porous material(s); and speed of liquid uptake, position within the assay device, and/or expansion properties of a compressed material. Depending on assay device feature selection, the timing between addition of fluid(s) from the fluid well(s) into the assay and the later addition of fluid from a capillary valve into the assay can occur with differences between five minutes and one hour without additional intervention by a user.

Assay devices can be modified as described with features depending on an intended environment for use of an assay device, such as expected humidity and temperature for an intended use case. In some embodiments, assay devices such as those described herein are intended for use in low resource settings, including use by mobile health care workers, use in emergency situations, and use at point of care remote health outposts or clinics. In some intended use cases, the assay devices will be used in non-climate controlled conditions with higher or lower temperature and humidity conditions than generally expected in climate-controlled buildings. Modifications can be made to assay device features in specific embodiments to compensate for intended use case environments and their effects on assay characteristics.

FIG. 1 depicts aspects of an assay device. The assay device 100 depicted in FIG. 1 is shown from a top-down viewpoint, such as a user might view the device at the start of an assay. The assay device includes a cassette 105, which is formed as an external shell around the internal assay components. The surface on the top of the cassette 105 of the assay device 100 is visible in the view of FIG. 1. For purposes of illustration and description herein the assay device 100 is shown with a first end 110 and a second end 120. Components of the assay device 100 that are positioned with a long axis parallel to the long axis of the cassette 105 are similarly described as having a first end and second end herein for consistent orientation description. Adjacent to the first end 110 is a fluid well 130 formed within the cassette 105. The fluid well 130 includes a lower aperture 135 within the fluid well 130. The fluid well 130 is of a size and shape to permit the flow of liquid through the aperture 135 to assay components within the cassette 105 interior. The assay device also includes a capillary valve 140 formed within the cassette 105. The capillary valve 140 includes a lower aperture 145 positioned within the cassette 105 interior. The assay device 100 includes a visualization aperture 150 within the cassette 105. In the viewpoint of FIG. 1, the visualization aperture 150 is the aperture in the top of the cassette 105 closest to the second end 120.

A cassette, as used herein, refers to a durable casing or shell surrounding other components of the assay. A cassette surrounds internal components, secures internal components in position relative to each other and the cassette, and provides structural features of an assay such as wells and apertures for the addition of reagents as well as detection of assay results by a user. A cassette can be manufactured from materials chosen for considerations such as durability, weight and cost. A cassette can be formed, for example, from a plastic material. In some embodiments, a cassette material has specific chemical properties at a surface to form functional capillary valves. For example, a cassette can be formed from cyclic olefin copolymer (COC), polymethyl methacrylate (PMMA), or polycarbonate (PC). The cassette is of a size and shape to surround other assay components. A cassette is formed with features of an appropriate size, shape and position relative to other assay components, such as the size, shape and position of fluid well(s), capillary valve(s), and a visualization aperture, as well as internal features. In some embodiments a cassette is formed from two parts which are of a size and shape to mate together into a full cassette. In some embodiments a cassette is formed from three or more parts which are of a size and shape to mate together to form a complete cassette.

Figure 2:
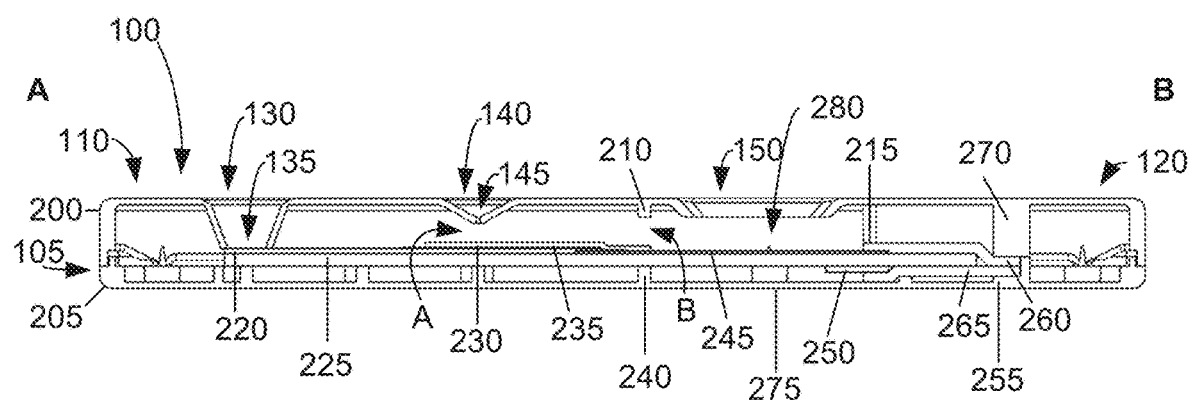
FIG. 2 is a cross section view of a cassette and internal assay components.

FIG. 2 illustrates an assay device 100 in a cross-section view in order to illustrate aspects of the interior of the assay device. The view shown in FIG. 2 relative to FIG. 1 depicts a cross-section view from position A at the first end 110 to position B at the second end 120 in the viewpoint of FIG. 1. The cassette 105 illustrated in FIG. 2 includes a top component 200 and a bottom component 205 which mate together to form the full cassette 105. The external surface at the lower wall 275 of the bottom component 205 is planar for stable positioning of the assay device 100 on a surface, such as a table or counter. The top component 200 of the cassette 105 includes a fluid well 130, a capillary valve 140 and a visualization aperture 150 formed from the cassette material.

A fluid well 130 is unitary with the cassette 105 and can be integrally formed of the same material as the remainder of the cassette, or a compatible material. Materials can be selected, for example, based on criteria including their manufacturability into a cassette structure, durability, weight and cost. The fluid well includes a top opening at the exterior surface of the cassette, the top opening of a size and shape to permit a user to add a reagent liquid, such as a sample liquid and/or a buffer liquid, to the fluid well. The fluid well 130 in the embodiment of FIG. 1 is positioned adjacent to the first end 110 of the cassette 105. The fluid well 130 includes a lower aperture 135 positioned within the interior of the cassette 105. The lower aperture of the fluid well is positioned adjacent to the surface of a porous sheet positioned to receive fluid from the aperture. In the embodiment depicted in FIG. 2, the lower aperture 135 of the fluid well 130 is positioned adjacent to the planar surface of a first porous sheet 220. During use, fluid would be added by a user to the fluid well 130 and flow through the lower aperture 135 into the first porous sheet 220. A fluid well is of a size and shape to carry a sufficient volume of fluid for assay functionality to the surface of the porous sheet adjacent to the lower aperture of the fluid well. The size, shape and position of the fluid well varies depending on the embodiment. In the embodiment shown in FIG. 2, the fluid well 130 is a substantially conical shape.

A capillary valve 140 is unitary with the cassette 105 and can be integrally formed of the same material as the remainder of the cassette, or a compatible material. Materials can be selected, for example, based on criteria including their surface-chemical interaction, contact angle for a specific geometry, manufacturability into a cassette structure, durability, weight and cost. The capillary valve 140 includes an aperture at the surface of the cassette 105 of a size, shape and position to permit a user to add reagent liquid to the capillary valve 140. The capillary valve includes a lower aperture positioned in alignment with the surface of a porous sheet separated from the lower aperture by a gap. In the embodiment illustrated in FIG. 2, the lower aperture 145 is positioned with gap A between the lower aperture 145 and a top surface of a third porous sheet 235. The capillary valve is of a size, shape, composition and position to hold a sufficient volume of liquid within the interior of the well until a top surface of a porous sheet moves to a position adjacent to the lower aperture of the capillary valve. The size, shape, composition and position of a capillary valve depends on the specific assay embodiment.

The size, shape, material and position of a capillary valve included in an assay device depends on the embodiment and the biochemical requirements of the fluids necessary for a specific assay to operate. The capillary valve forms a microchannel that includes either a specific geometry and/or surface-chemical interaction with the assay fluid within the interior of the capillary valve to hold the fluid within the capillary valve. In some embodiments, the capillary valve is shaped as a circular tube with an abrupt end at the lower aperture due to change geometry. A variation of the Young-Laplace equation can be used to calculate the fluid equilibrium pressure at the lower aperture, and therefore the conditions required to maintain the fluid within the interior of the capillary valve until a surface of a porous sheet moves across the gap to an adjacent position to the lower aperture of the capillary valve to permit fluid flow into the porous sheet. The diameter, interior volume and contact angle at the lower aperture can be calculated to determine the size and shape of a capillary valve for a given embodiment. See, e.g.: Cho et al., "How the capillary burst microvalve works," *J. Colloid Interface Sci.*, vol. 306, no. 2, pp. 379-385, February 2007; Roy et al., "High performance of cyclic olefin copolymer-based capillary electrophoretic chips," *ACS Appl. Mater. Interfaces*, vol. 5, no. 12, pp. 5683-5689, June 2013; and Rymuszka et al., "Wettability and thermal analysis of hydrophobic poly(methyl methacrylate)/silica nanocomposites," *Adsorpt. Sci. Technol.*, vol. 35, no. 5-6, pp. 560-571, June 2017; each of which are hereby incorporated by reference. See also "Critical Surface Tension and Contact Angle with Water for Various Polymers (sort by contact angle)" available online from Accu Dyne Test, the version accessed May 19, 2020 is incorporated herein by reference.

Depending on the embodiment, the size of a gap between a lower aperture of a capillary valve and the top surface of a porous sheet ranges from 2 mm to 5 cm. In order to fit within a standard cassette, the gap size is generally intended to be between 2 mm and one cm. In some embodiments, a gap size is greater than one cm as required by a specific assay and/or intended use situation. Generally, a larger gap creates a longer delay between fluid moving through the fluid well(s) and the addition of fluid from a capillary valve to an assay. Assay devices with expected delay times can be manufactured as required by the stages or steps of an implemented biochemical assay.

During implementation of an assay, a user can add appropriate liquids to the fluid well(s) and the capillary valve of an assay device at a start time. Liquid added to the fluid well(s) will flow quickly through the lower aperture(s) of the well(s) into the adjacent porous sheet(s) and flow though the interior of the assay. Liquid added to the capillary valve can be added at the assay start time but will be held within the interior of the capillary valve until a later time when the upper surface of the porous sheet, originally separated by a gap from the lower aperture of the capillary valve, moves to be adjacent to the lower aperture, at that later time the liquid will flow through the lower aperture and into the then-adjacent porous sheet. A user, therefore, does not need to monitor the assay device and add a second buffer or reagent liquid at a preset time interval after the assay start time. The ease of use is envisioned to improve operability of the assay device, particularly in situations where the user has multiple competing tasks and/or where the user is minimally trained or has little experience with similar assay procedures.

The cassette 105 includes a visualization aperture 150 in the top component 200 of the cassette 105. The visualization aperture 150 is positioned to permit a user to see a visual change, such as a color change, in a porous material within the assay device structure as a readout of the assay results. The visualization aperture is in alignment with a top surface of a porous sheet including reagents that create a color or other visual change in the surface during the assay. For example, the embodiment of FIG. 2 depicts the top surface of the second porous sheet 145 is in alignment with the visualization aperture 150 and includes a reagent 280 affixed to the surface. A reagent can include, for example, an antibody, a protein, and/or a nucleic acid as required by the biochemistry of a specific assay. In some embodiments, the visualization aperture is of a size and shape to interface with a camera device, such as a cell phone camera. In some embodiments, the visualization aperture is of a size and shape to interface with an assay reader device. The visualization aperture 150 in the embodiment illustrated in FIG. 2 is positioned adjacent to the second end 120 of the device, and of a size and shape so that a user can visualize changes in the surface of the second porous sheet 245 adjacent to the visualization aperture 150.

FIG. 2 depicts an embodiment of an assay device 100 that includes a first porous sheet 220, and a second porous sheet 245 positioned so that the first end of the second porous sheet 245 is adjacent to the second end of the first porous sheet 220. A third porous sheet 235 overlays the second end of the first porous sheet 220 and the first end of the second porous sheet 245. A moisture barrier 230 is positioned underneath the third porous sheet 235, so the lower surface of the third porous sheet 235 does not contact the top surface of the first porous sheet 220. Depending on the embodiment, a moisture barrier can be fabricated from materials such as a thin plastic sheet, mylar or metal film. In some embodiments a moisture barrier can include an adhesive to secure the moisture barrier relative to the adjacent porous sheets. The moisture barrier 230 is positioned so that the second porous sheet 245 contacts the third porous sheet 235 at the second end of the second porous sheet 245. The third porous sheet 235 overlays the second porous sheet 245 at a position that is not adjacent to the visualization aperture 150, so the second porous sheet 245 surface is beneath the visualization aperture 150.

A porous sheet, as used herein, includes materials formed as substantially planar sheet structures that permit the flow of liquid within the internal structure. For example, in some embodiments a porous sheet can include a glass fiber material or a nitrocellulose material. A porous sheet can include reagents for a biochemical assay to be carried out by the assay device, for example reagents including embedded salts, antibody conjugates, and/or nucleic acids. A porous sheet can include one or more types of binding proteins, such as antibodies or aptamers. In some embodiments, a porous sheet includes visual amplification reagents in a dry form, such as enzymes (e.g. horseradish peroxidase, or alkaline phosphatase), developing reagents such as 3,3 diaminobenzedene (DAB) or silver enhancement reagents. In some embodiments, reagents for a nucleic acid amplification reaction can be stored in one or more porous sheets. Reagents for a nucleic acid amplification reaction include enzymes, such as DNA polymerase, as well as nucleic acids of known sequence (e.g. primers and/or probes for a specific amplification assay). A porous sheet can also include stabilizing agents such as sugars like trehalose or sucrose, and protein blockers such as bovine serum albumin (BSA) or casein. In embodiments that include multiple porous sheets, the capillary pressure of the porous materials should increase or be maintained through the expected liquid flow path. For example, a first porous sheet can have a lower capillary pressure than a second porous sheet. For example, a second porous sheet can have a lower capillary pressure than a third porous sheet. A porous sheet should be manufactured from a material that is hydrophilic, or the porous sheet can be treated so that the sheet becomes hydrophilic.

The assay device includes a wicking material in contact with the second end of the porous sheet at the second end of the assay device. In the embodiment illustrated in FIG. 2, the assay device 100 includes a wicking material made of two parts in physical contact with each other. The first part 260 of the wicking material has a first end in contact with the second end of the third porous sheet 235. The second end of the first part 260 of the wicking material is in contact with the second part 265 of the wicking material, so that the combined ends of the first part 260 and the second part 265 of the wicking material wrap around the second end of the third porous sheet 235. A compressed material 250 is positioned adjacent to the second part 265 of the wicking material, underneath the third porous sheet 235.

A wicking material, as used herein, includes a material that can absorb liquid flowing through the assay components within an assay device. A wicking material has a capillary pressure greater than that of the adjacent porous sheet, which is in contact with the wicking material. For example, a wicking material can include a cellulose material. In some embodiments, the wicking material is a single piece of material that can wrap around the second end of the porous sheet and support material. The length of the wicking material will depend on a specific embodiment and can be adjusted as needed for a time delay between steps or stages of an assay.

A compressed material, as used herein, includes a material that is a smaller size when it is substantially dry than when it is substantially wet, so that the compressed material expands within the assay device and moves other components of the assay device. A compressed material has a reduced size when not holding liquid and a larger size when it is holding liquid. For example, depending on the embodiment a compressed material can include a compressed cellulose sponge, a hydrogel or a sufficiently absorbing polymer. The expansion properties of a compressed material can be selected for a specific embodiment, for example the size change in a particular period of time and/or the maximum size change of a compressed material.

The assay device 100 includes features to maintain the position of the assay components relative to each other within the cassette 105. The relative position of the assay components is required for function of the assay, as described herein. A support material 225 underlays the first porous sheet 220, the second porous sheet 245, the third porous sheet 235 and the moisture barrier 230. The support material 225 can be, for example, a flexible plastic sheet or a moisture-impenetrable card. The support material can include an adhesive to secure the support material to the adjacent porous sheet(s) and wicking material. In the embodiment illustrated in FIG. 2, the top component 200 of the cassette 105 includes a mechanical pivot 215 which projects from the interior surface of the top component 200 adjacent to the second end of the visualization aperture 150. The distal end of the mechanical pivot 215 is positioned adjacent to a top surface of the wicking material 260 at the first end, so that the mechanical pivot 215 secures the relative position of the wicking material. The compressed material 250 has a first end at a position aligned with the first end 110 of the assay device 105 from the mechanical pivot 215. The compressed material 250 will, therefore, expand toward the first end 110 of the device after absorbing liquid.

At the second end 120 of the cassette 105, the top component 200 includes a top mechanical compression projection 270 that is positioned between the top internal surface of the top component 200 of the cassette 105 and the top surface of the wicking material 260. The bottom component 205 includes a corresponding bottom mechanical compression projection 255 that is positioned between the internal surface of the bottom component 205 and the lower surface of the wicking material 265. The combined mechanical compression projections 270, 255 secure the wicking material 260, 265 in position within the cassette 105 interior.

The top component 200 of the cassette 105 includes a top mechanical pivot 210 which projects downwards from the top interior surface towards the top surface of the second end of the third porous sheet 235. A gap B is between the distal end of the mechanical pivot 210 and the surface of the third porous sheet 235. A corresponding lower mechanical pivot 240 projects upwards from the internal surface of the bottom component 205. During use of the assay device, the compressed material expands after absorbing liquid from the assay reagents. The resulting expansion forces the support material 225 and the porous sheets 220, 245, 235 away from the bottom component of the cassette 205 and toward the top component 200. The lower surface of the upper mechanical pivot 210 controls this movement so that the third porous sheet 235, which is substantially to the first end of the mechanical pivot 210, moves to be adjacent to the lower aperture 145 of the capillary valve 140 and permits fluid flow from the interior of the capillary valve 140 into the third porous sheet 245. The resulting effect is a second fluid flow into the assay within the assay device, the second fluid flow occurring at a predetermined time period after the initiation of the assay without further intervention by a user.

In some embodiments, an assay device can include one porous sheet, two porous sheets, or three porous sheets as described herein. Similarly depending on the embodiment an assay device can include a single fluid well and a single capillary valve, or two fluid wells and a single capillary valve. Some embodiments include multiple capillary valves. The selection of numbers, size, position and compositions of porous sheets, fluid wells and capillary valves depends on the biochemical requirements of a specific assay implementation and intended use case.

In some embodiments, an assay device includes: a cassette, including an upper component with a fluid well, a capillary valve, a top section of a mechanical stop region, a top section of a mechanical compression region, and a visualization aperture, a lower component with a bottom portion of the mechanical stop region and a bottom portion of the mechanical compression region; and a set of assay components, including a porous sheet with a first end and a second end, a wicking material in contact with the second end of the porous sheet, and a compressed material of a size, shape and position to expand sufficiently when wet to move a top surface of the porous sheet adjacent to an aperture of the capillary valve.

Figure 3:
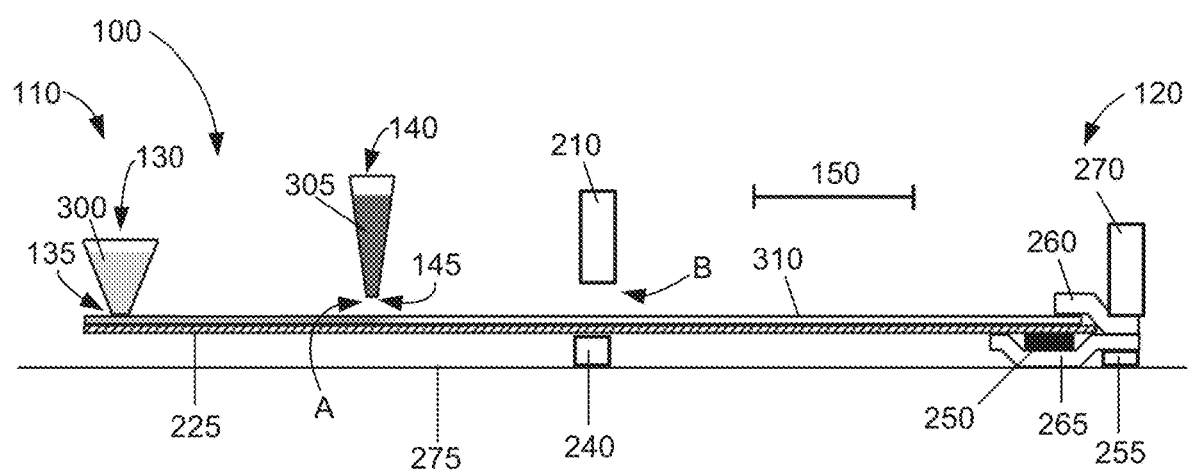
FIG. 3 is a cross section view of some features of a cassette and internal assay components.

FIG. 3 depicts aspects of an assay device 100. FIG. 3 illustrates a simplified version of an assay device with only some components depicted. For example, for clearer presentation the cassette shell has been largely removed from the illustration shown in in FIG. 3. The lower wall 275 of the cassette is depicted for context.

FIG. 3 shows aspects of an assay device 100 at the start of an assay, at the time point directly after a user has added a sample fluid 300 to the fluid well 130 and a reagent fluid 305 to the capillary valve 140. Depending on the biochemical assay the sample fluid can include a sample for testing as well as a buffer solution and/or further reagents. A reagent fluid within the capillary valve can include reagents needed for subsequent portions of the biochemical assay. In some embodiments, a sample fluid and/or a reagent fluid can be an aqueous solution that includes buffering reagents for the assay, such as phosphate buffered saline, borate or tris HCL. In some embodiments, a sample fluid and/or a reagent fluid can include one or more blocking agents such as bovine serum albumin (BSA) or casein. In some embodiments, a sample fluid and/or a reagent fluid can include a surfactant such as triton X-100, tween 20, or tween 80.

In the embodiment illustrated in FIG. 3, the assay includes a single porous sheet 310. A support material 225 underlays the porous sheet 310. The sample fluid 300 moves into the porous sheet 310 through the lower aperture 135 of the fluid well 130 immediately after addition by a user, as illustrated with the color gradient within the porous sheet near the first end. The reagent fluid 305 within the capillary valve 140 does not move through the lower aperture 145 immediately at the start of the assay, but is initially maintained within the capillary valve 140. The gap A separates the lower aperture 145 from the porous sheet 310. The compressed material 250 is positioned adjacent to the bottom surface of the porous sheet 310 and in contact with the wicking material 265, while the support material 225 is positioned between the bottom surface of the porous sheet 310 and the compressed material 250.

Figure 4:
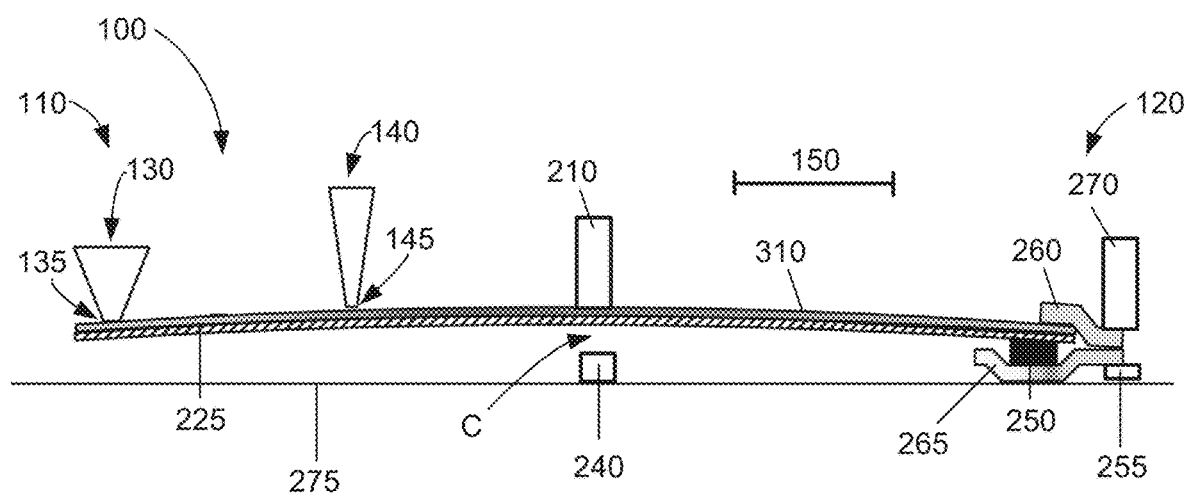
FIG. 4 is a cross section view of some features of a cassette and internal assay components.

FIG. 4 depicts a later time point in an assay utilizing an assay device 100 such as shown in FIG. 3. FIG. 4 illustrates a time point wherein the sample fluid has moved from the interior of the fluid well 130 through the lower aperture 135 and along the length of the porous sheet 310 into the wicking material 260, 265. From the wicking material 260, 265 the fluid has moved into the compressed material 250. Uptake of the fluid has caused the compressed material 250 to expand, pushing upwards from the lower section of wicking material 265 against the lower wall 275 of the cassette and moving the support material 225 upwards. This movement is constrained by the mechanical pivot 210 on the top surface, with the gap C opening between the lower mechanical pivot 240 and the lower surface of the support material 225. The wicking material 260, 265 is secured in position with the mechanical compression projections 270, 255 of the cassette. The top section of the mechanical compression region 270 is positioned adjacent to a top surface of the wicking material 260 and the bottom portion of the mechanical compression region 255 is positioned adjacent to a bottom surface of the wicking material 265 within the cassette. The porous sheet 310 has moved to the point where its upper surface is positioned adjacent to the lower aperture 145 of the capillary valve 140, so that the reagent fluid that was within the capillary valve 140 (see FIG. 3) has moved through the lower aperture 145 into the porous sheet 310. In this manner, the reagent fluid has been delivered to the porous sheet at a time period after the initial addition of both the buffer fluid and the reagent fluid to the assay by a user (e.g. as depicted in FIG. 3). The visual output of the assay device can be seen by a user through the visualization aperture 150.

The relative timing of fluids passing from the fluid well(s) and capillary valve(s) into a porous sheet of an assay can be adjusted relative to the needs of a particular assay embodiment. For example the length, thickness and material composition of the porous sheet(s) can be selected with known fluid flow characteristics and the amount of time for a volume of sample fluid to move from a fluid well to the second end of the porous sheet(s) can be calculated and adjusted for a particular assay. Similarly the absorbance characteristics, size, shape and position of a wicking material can be adjusted to change the amount of time a fluid will take to pass through the wicking material and into the compressed material. Additionally, the composition, size, shape and position of a compressed material can be adjusted for a specific time and rate of expansion. For example, various embodiments can include time delays between steps or stages of an assay in the range between 5 minutes and 60 minutes (one hour). For example, an assay embodiment using horseradish peroxidase and diaminobenzidine as signal enhancement agents can require 15 minutes of delay between stages of the assay.

In some embodiments, an assay device includes: a cassette, including an upper component with a fluid well, a capillary valve, a top section of a mechanical stop region, a top section of a mechanical compression region, and a visualization aperture, a lower component with a bottom portion of the mechanical stop region and a bottom portion of the mechanical compression region; and a set of assay components, including a first porous sheet with a first end and a second end, a second porous sheet with a first end and a second end, wherein the second end of the first porous sheet is in contact with the first end of the second porous sheet, a wicking material in contact with the second end of the second porous sheet, and a compressed material of a size, shape and position to expand sufficiently when wet to move a top surface of the porous sheet adjacent to an aperture of the capillary valve.

Figure 5:
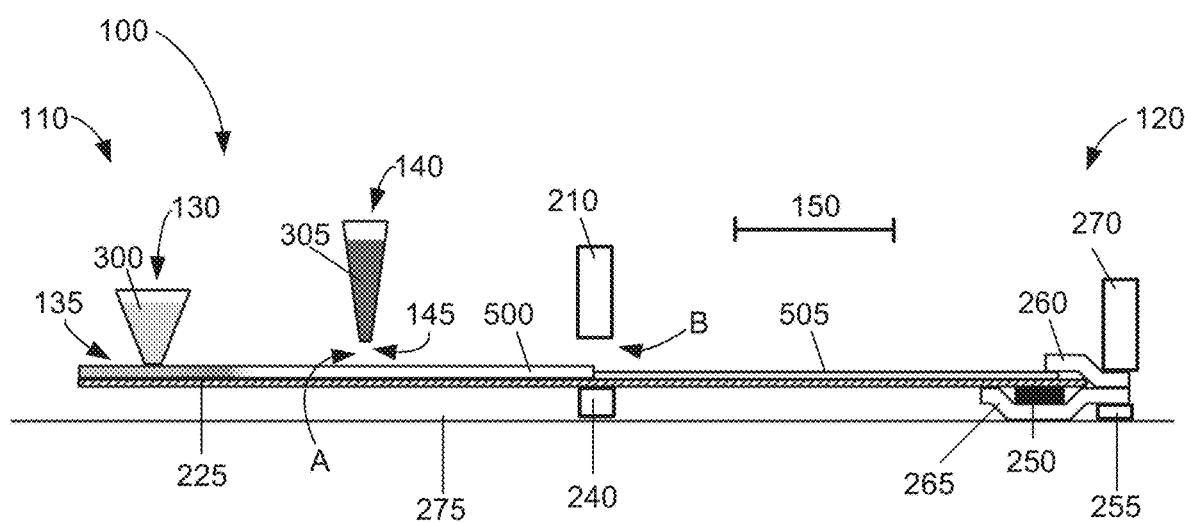
FIG. 5 is a cross section view of some features of a cassette and internal assay components.

FIG. 5 depicts aspects of an assay device 100, with some features removed to improve clarity. The assay device includes a first porous sheet 500, with a first end corresponding to the first end 110 of the assay device and a second end. The first porous sheet 500 is positioned in a linear array with a second porous sheet 505. The second end of the first porous sheet 500 is in contact with the first end of the second porous sheet 505. The first porous sheet has a capillary pressure less than or equal to that of the second porous sheet. The support material 225 is positioned underneath both the first porous sheet 500 and the second porous sheet 505. The mechanical pivot 210, 240 projections from the interior of the cassette inward are positioned adjacent to the junction where the first porous sheet 500 and the second porous sheet 505 contact each other. A gap B is located between the lower end of the top mechanical pivot 210 and the top surface of the first porous sheet 500 and the second porous sheet 505. Similarly to FIG. 3, at the time illustrated in FIG. 5 the sample fluid 300 has just been added to the fluid well 130 and is moving through the lower aperture 135 of the fluid well 130 into the first end of the first porous sheet. The fluid flow of the sample fluid 300 is along the length of the first porous sheet 500 from the first end to the second end, wherein it will move into the second porous sheet 505 at the first end. The reagent fluid 305 is maintained within the capillary valve 140, with a gap A between the lower aperture 145 of the capillary valve 140 and the top surface of the first porous sheet 500. A visualization aperture 150 is positioned above the second porous sheet 505.

Figure 6:
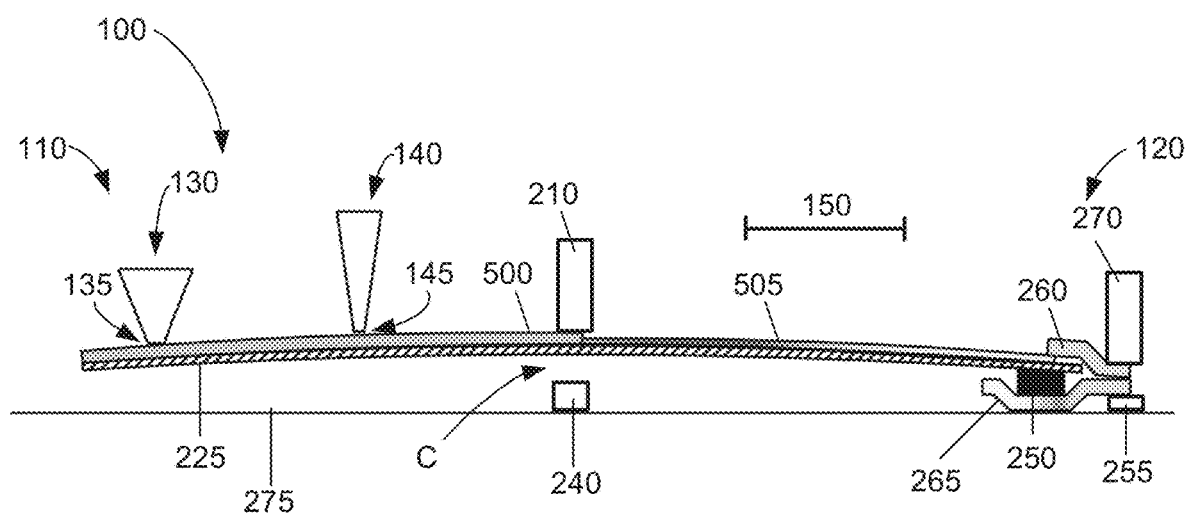
FIG. 6 is a cross section view of some features of a cassette and internal assay components.

FIG. 6 depicts an assay device 100 similar to the one shown in FIG. 5 at a later time point of the assay. The sample fluid has moved into the first porous sheet 500, along the length of the first porous sheet 500 to the second end, and into the first end of the second porous sheet 505. The sample fluid has moved along the length of the second porous sheet 505 to the second end, and into the wicking material 260, 265. From the wicking material 260, 265 the sample fluid has moved into the compressed material 250, causing it to expand. The expansion presses upward on the support material 225, which moves the first porous sheet 500 and the second porous sheet 505 upward (e.g. away from the lower wall 275 of the cassette). The end of the top mechanical pivot 210 is in contact with the junction between the first porous sheet 500 and the second porous sheet 505, holding the sheets in relative position. A new gap C has opened up between the lower surface of the support material 225 and the lower mechanical pivot 240. The lower aperture 145 of the capillary valve 140 is now in position adjacent to the top surface of the first porous sheet 500, so the reagent fluid has moved through the lower aperture 145 and into the first porous sheet 500. From there the reagent fluid will follow a similar fluid path to the sample fluid, through the first porous sheet 500 to its second end and into the first end of the second porous sheet 505. The reagent fluid can subsequently react with the biochemical components present in the second porous sheet as part of the assay operation.

In some embodiments, an assay device includes: a cassette, including an upper component with a fluid well, a capillary valve, a top section of a mechanical stop region, a top section of a mechanical compression region, and a visualization aperture, a lower component with a bottom portion of the mechanical stop region and a bottom portion of the mechanical compression region; and a set of assay components, including a first porous sheet with a first end and a second end, a second porous sheet with a first end and a second end, a third porous sheet with a first end and a second end, wherein the second porous sheet overlays the second end of the first porous sheet and the first end of the third porous sheet, a wicking material in contact with the second end of the third porous sheet, and a compressed material of a size, shape and position to expand sufficiently when wet to move a top surface of the second porous sheet adjacent to an aperture of the capillary valve.

Figure 7:
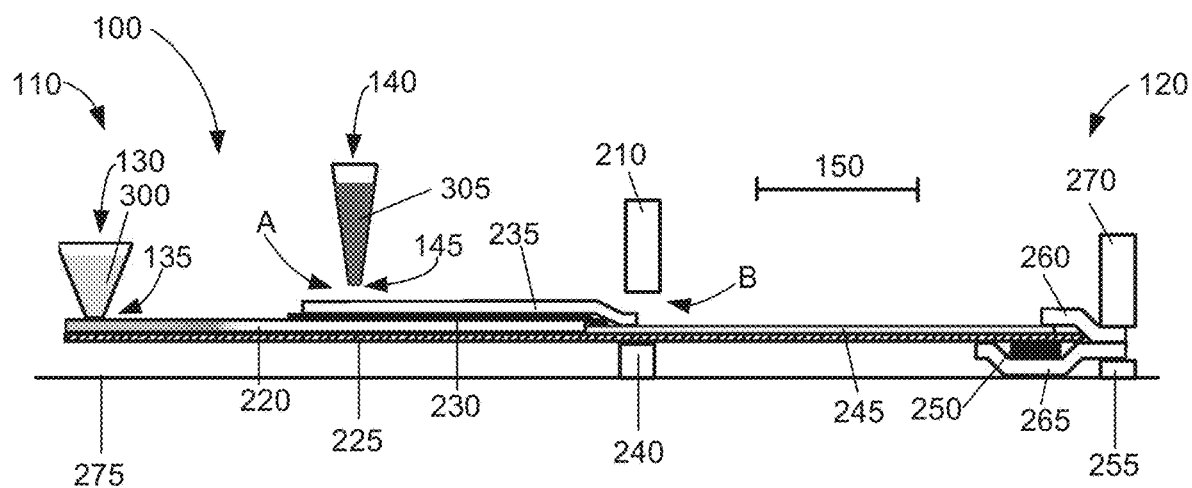
FIG. 7 is a cross section view of some features of a cassette and internal assay components.

FIG. 7 depicts aspects of an assay device 100, with some features removed for illustration purposes. The device 100 is similar to that depicted in FIG. 2, with the cassette shell mostly removed for purposes of illustration. The assay device 100 includes a first porous sheet 220, a second porous sheet 245 and a third porous sheet 235 partially overlaying the first porous sheet 220 and the second porous sheet 245. A moisture barrier 230 is positioned between the third porous sheet 235 and the first porous sheet 220. The moisture barrier 230 is also positioned over the junction contacting the first porous sheet 220 and the second porous sheet 245, separating them from the overlaying third porous sheet 235. The second end of the third porous sheet 235 extends beyond the second end of the moisture barrier 230 and contacts the top surface of the second porous sheet 245 at a position in alignment with the mechanical pivot 210, 240. The assay device 100 shown in FIG. 7 has sample fluid 300 added to the fluid well 130. The sample fluid 300 is moving though the lower aperture 135 of the fluid well 130 into the first porous sheet 220, illustrated by the color gradient in the first porous sheet 220. The fluid is moving from the first end of the first porous sheet 220 towards the second end of the first porous sheet 220. It will travel across the junction between the first porous sheet 220 and the second porous sheet 245, into the wicking material 260, 265 and further into the compressed material 250. The capillary pressure of the second porous sheet is greater than that of the third porous sheet, inhibiting fluid movement from the second porous sheet into the third porous sheet. The reagent fluid 305 was added to the capillary valve 140 at a similar time as the sample fluid 300 to the fluid well 130. The reagent fluid 305 is maintained within the capillary valve 140.

Figure 8:
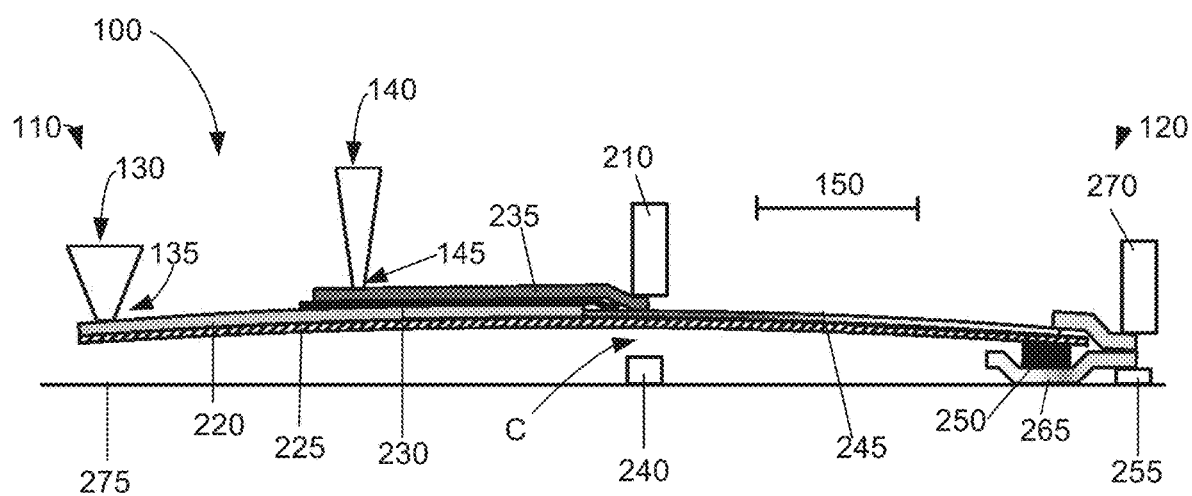
FIG. 8 is a cross section view of some features of a cassette and internal assay components.

FIG. 8 depicts an assay device 100 similar to the one shown in FIG. 7 at a later time point in the assay. The sample fluid has moved into the compressed material 250 as described relative to FIG. 7, causing the compressed material 250 to expand upwards against the support material 225. This moves the second end of the third porous sheet 235 upwards against the lower face of the mechanical pivot 210, leaving a gap C between the top face of the lower mechanical pivot 240 and the lower surface of the support material 225. The lower aperture 145 of the capillary valve 140 is now adjacent to the top surface of the first end of the third porous sheet 235, and the reagent fluid has moved into the third porous sheet 235. Since the capillary pressure of the third porous sheet 235 is less than or equal to that of the second porous sheet 245, the fluid will flow into the second porous sheet 245, resulting in a biochemical reaction within the second porous sheet 245. A resulting visual change in the second porous sheet 245 is visible to a user through the visualization aperture 150.

Figure 9:
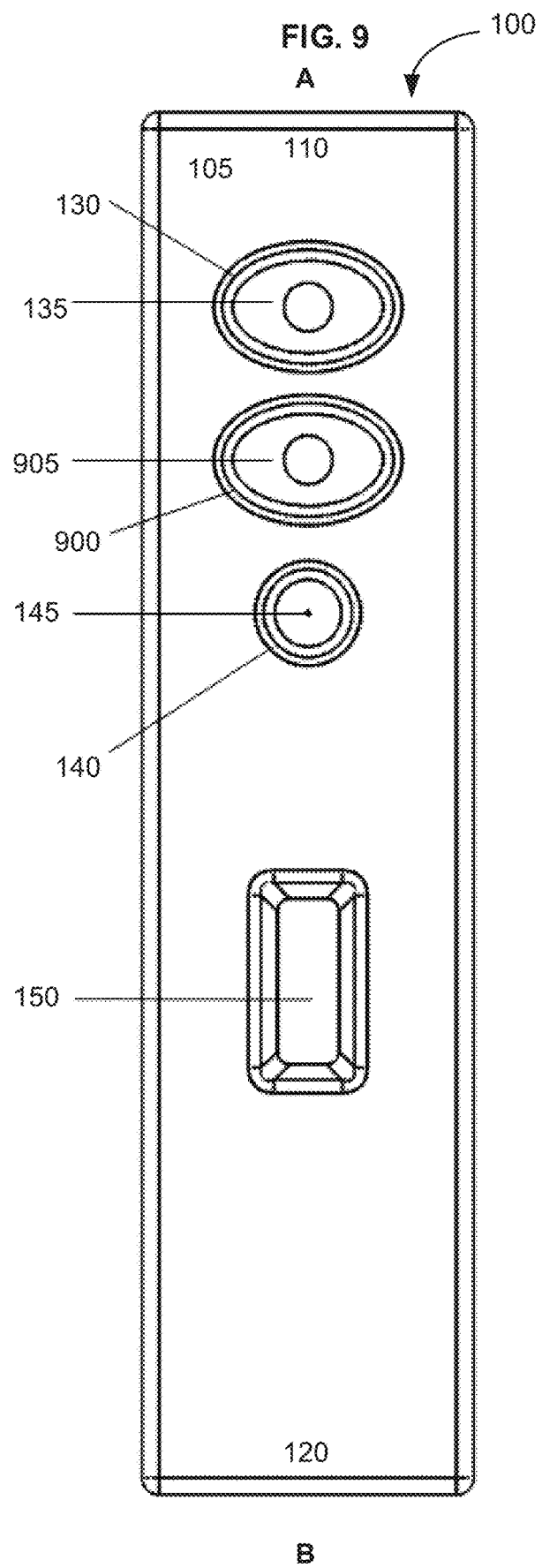
FIG. 9 is an external view of the top cassette face of an assay device.

FIG. 9 depicts an assay device 100 from a top down viewpoint, as might be seen by a user during implementation of an assay. The assay device 100 includes a cassette 105, with a first end 110 and a second end 120 noted for orientation purposes. The assay device 100 includes a first fluid well 130 with a lower aperture 135 positioned within the interior of the cassette in alignment with internal features of the assay device 100. The assay device 100 includes a second fluid well 900, with a lower aperture 905 positioned within the interior of the cassette in alignment with internal features of the assay device 100. Also visible is a capillary valve 140 with a lower aperture 145 positioned within the interior of the cassette in alignment with internal features of the assay device 100. The assay device 100 includes a visualization aperture 150 which aligns with interior features of the assay.

Figure 10:
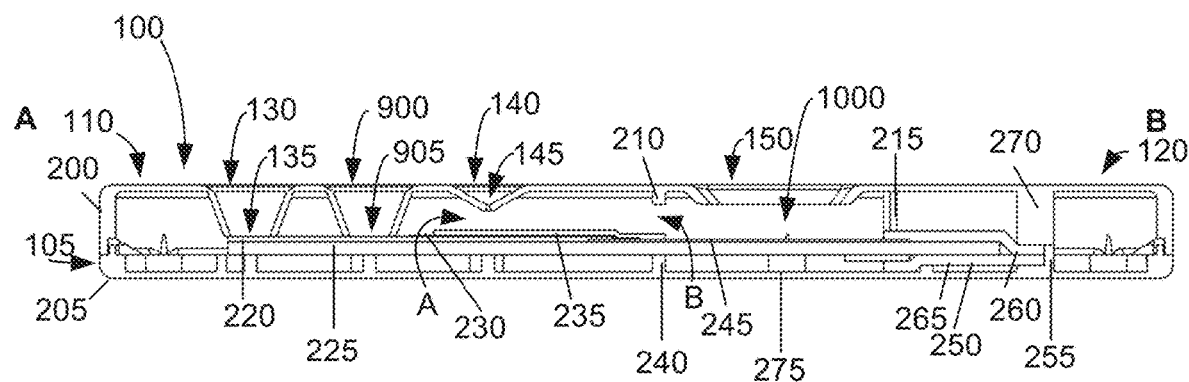
FIG. 10 is a cross section view of a cassette and internal assay components.

FIG. 10 depicts an assay device 100 similar to the one shown in FIG. 9, in a cross-section view. The assay device in FIG. 10 is a cross section view from approximately A to B relative to FIG. 9. A first fluid well 130 is positioned adjacent to the first end 110 of the device 100, with the lower aperture 135 of the first fluid well 130 positioned adjacent to the upper surface of a first end of a first porous sheet 220 within the cassette. The assay device 100 includes a second fluid well 900 at a position closer to the second end 120 of the device than the first fluid well 130. The second fluid well 900 includes a lower aperture 905 positioned adjacent to the upper surface of the first porous sheet 220. A capillary valve 140 has a lower aperture 145 aligned with a top surface of the third porous sheet 235, with a gap A between the lower aperture 145 and the top surface of the third porous sheet 235. A visualization aperture 150 is positioned in alignment with the top surface of the second porous sheet 245. The second porous sheet 245 includes a reagent 1000 attached to the upper surface in alignment with the visualization aperture 150. During implementation of the assay, a reagent 1000 can, for example, anchor other biochemical components of the assay to create a color change visible to a user of the assay. For example a reagent 1000 can include an antibody, an aptamer, a nucleic acid and/or a protein. For example, an antibody can include a complete antibody, IgG, IgM or an antibody fragment such as a Fc, Fab, Fv or similar antibody fragment.

Figure 11:
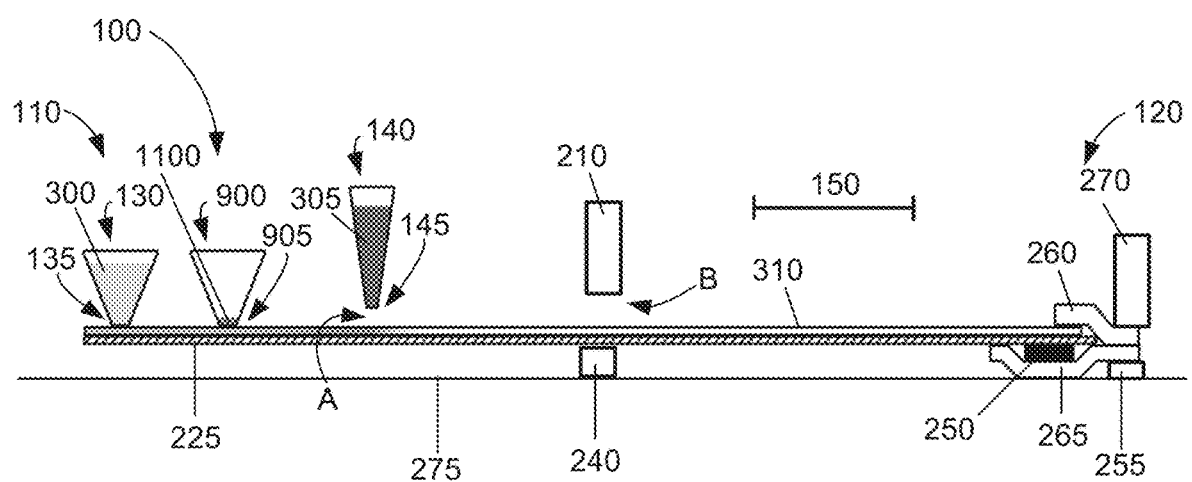
FIG. 11 is a cross section view of some features of a cassette and internal assay components.

FIG. 11 depicts aspects of an assay device 100 that incorporates a single porous sheet 310 and both a first fluid well 130 and a second fluid well 900. Most of the cassette has been removed from the illustration of FIG. 11 for clarity, although the lower wall 275 of the cassette is shown for reference. FIG. 11 illustrates an assay device 100 with a first end 110 and a second end 120, with a first fluid well 130 positioned adjacent to the first end 110 and a second fluid well 900 to the second end position relative to the first well 130. A capillary valve 140 is farther towards the second end 120 of the cassette relative to the first fluid well 130 and the second fluid well 900. At the time illustrated, a user has added a first fluid 300 to the first fluid well 130 and a second fluid 1100 to the second fluid well 900. The first fluid and the second fluid, depending on the specific assay, can include assay reagents and the sample being tested. In some embodiments, a first well can be used to add liquid sample to an assay, and a second well can be used to add a buffer liquid to the assay. In some embodiments it can be helpful to have a first well and a second well appropriately labelled on the exterior surface of the cassette, for example as "sample" and "buffer" for clarity and ease of use. The first fluid 300 and the second fluid 900 move through the lower apertures 135, 905 of the first fluid well 130 and the second fluid well 900 respectively, and flow into the porous sheet 310. This is visualized by the color gradient in the porous sheet 310 depicted in FIG. 11. The first fluid and second fluid mix within the porous sheet, as desired by the biochemistry of a specific assay incorporated into the device. The porous sheet 310 has a lower capillary pressure than the wicking material 260, 265 which will draw the fluid through the porous sheet 310 into the wicking material over the duration of the assay progression.

At the stage illustrated in FIG. 11, a reagent fluid 305 has been added by a user to the capillary valve 140 and is held within the capillary valve 140. The lower aperture 145 of the capillary valve 140 is positioned with a gap A between the lower aperture 145 and the top surface of the porous sheet 310. There is a gap B between the lower face of the upper mechanical pivot 210 and the top surface of the porous sheet 310.

Figure 12:
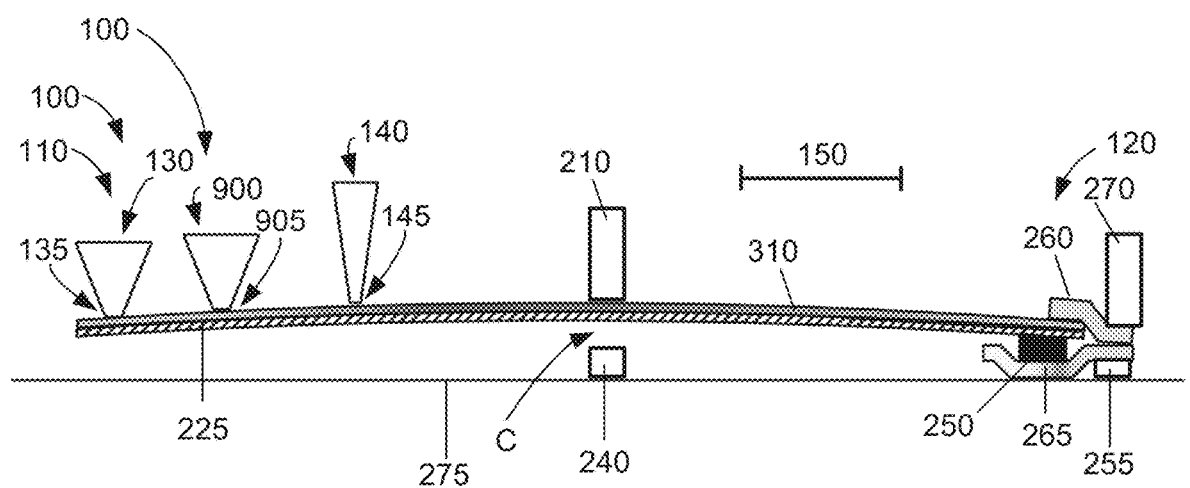
FIG. 12 is a cross section view of some features of a cassette and internal assay components.

FIG. 12 depicts aspects of an assay device 100 similar to the one shown in FIG. 11 at a later time point in the assay progression. In the view of FIG. 12, the first fluid 300 and the second fluid 900 have entirely moved through the lower apertures 135, 905 of the first fluid well 130 and the second fluid well 900 respectively into the porous sheet 310. This fluid is depicted with the color gradient in the porous sheet 310. The fluid has moved into the wicking material 260, 265, as depicted by the color gradient therein, and further into the compressed material 250. The compressed material 250 has expanded, pushing upwards from the wicking material 265 positioned against the lower wall 275 of the cassette and moving the support material 225 and the porous sheet 310 upwards. The movement of the porous sheet 310 and the support material 225 upwards is inhibited by the lower surface of the upper mechanical pivot 210. A gap C has correspondingly opened between the lower surface of the support material 225 and the lower mechanical pivot 240. The lower aperture 145 of the capillary valve 140 is now positioned adjacent to the upper surface of the porous sheet 310. The reagent fluid that was held within the capillary valve 140 has moved through the lower aperture 145 and into the porous sheet, mixing with the first fluid and the second fluid within the porous sheet. This mixture of fluids will flow through the porous sheet 310 towards the second end 120, and a resulting color change depicting the results of the assay can be visualized by a user through the visualization aperture 510.

Figure 13:
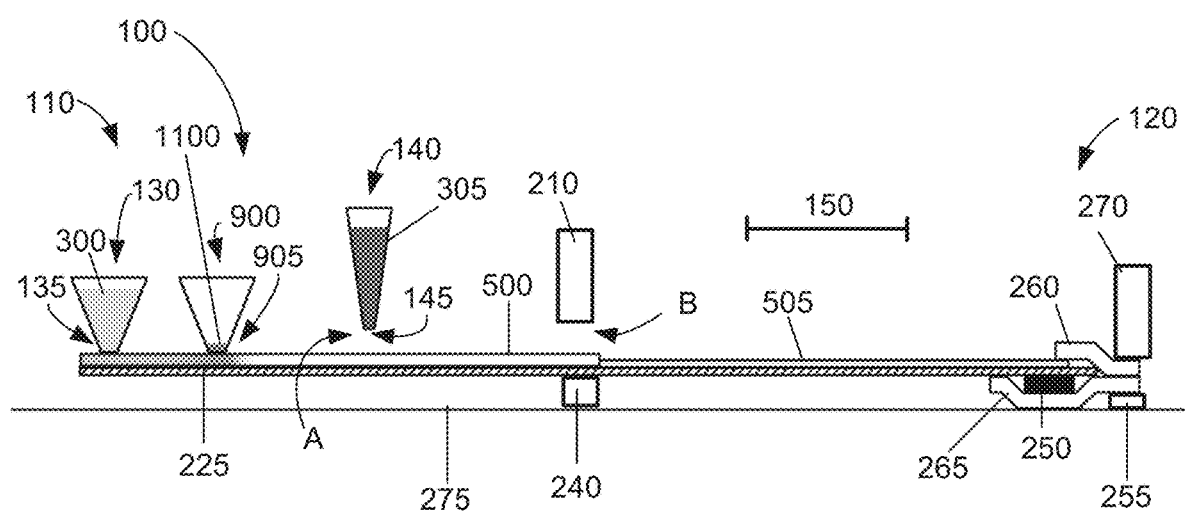
FIG. 13 is a cross section view of some features of a cassette and internal assay components.

FIG. 13 depicts aspects of an assay device 100. The assay device 100 includes a first porous sheet 500 and a second porous sheet 505 aligned linearly relative to each other. The first porous sheet 500 has a lower capillary pressure than the second porous sheet 505. The second porous sheet 505 has a lower capillary pressure than the wicking material 260, 265. As a result, fluid flow moves from the first end 110 to the second end 120 of the assay device 100. At the timepoint shown in FIG. 13, a user has added fluids appropriate to the assay to the first fluid well 130, the second fluid well 900 and the capillary valve 140. The fluids 300, 1100 within the first fluid well 130 and the second fluid well 900 are flowing through the respective lower apertures 135, 905 and into the first porous sheet 500. FIG. 13 depicts this fluid flow with a color gradient within the first porous sheet 500. A reagent fluid 305 has been added by a user to the capillary valve 140 and is held within the capillary valve 140. The lower aperture 145 of the capillary valve 140 is positioned with a gap A between the lower aperture 145 and the top surface of the first porous sheet 500. There is a gap B between the lower face of the upper mechanical pivot 210 and the top surface of the first porous sheet 500 at a position adjacent to the second end of the first porous sheet 500. A visualization aperture 150 is positioned above the top surface of the second porous sheet 505 at a location where a user can detect the results of the assay on the second porous sheet 505.

Figure 14:
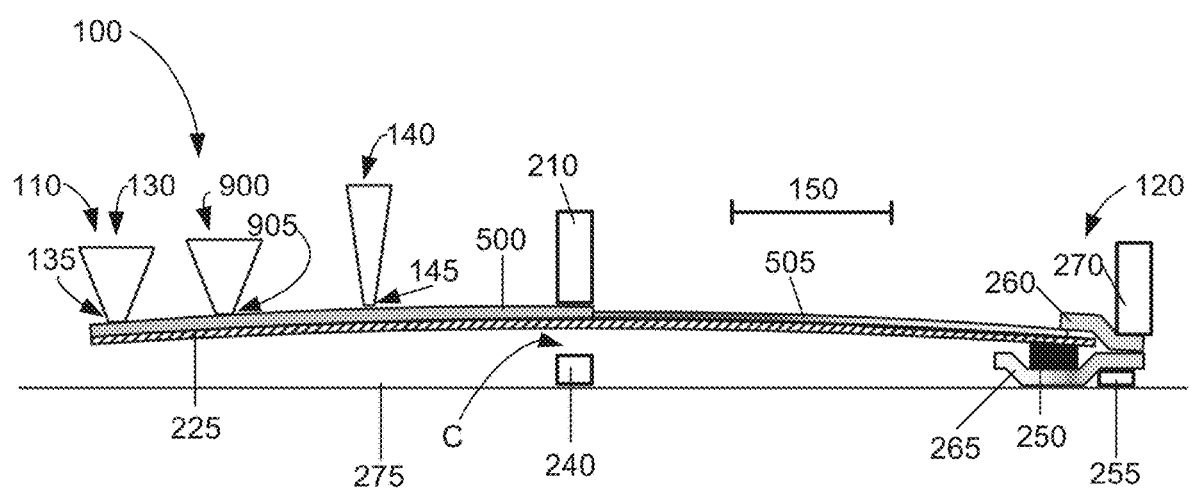
FIG. 14 is a cross section view of some features of a cassette and internal assay components.

FIG. 14 depicts aspects of an assay device 100 during an assay, the assay device 100 is similar to the one shown in FIG. 13 at a later timepoint in the assay progression. The fluids that were within the first fluid well 130 and the second fluid well 900 have moved through the respective lower apertures 135, 905 of the fluid wells 130, 900 and into the first porous sheet 500, as shown by the color gradient within the first porous sheet 500. The fluids have mixed within the porous sheet 500 and moved through the junction at the second end of the first porous sheet 500 into the first end of the second porous sheet 505, as shown by the color gradient within the second porous sheet 505. The fluids have mixed with whatever reagents were embedded in both the first porous sheet and second porous sheet as specific to the biochemical assay. The fluids have moved into the wicking material 260, 265 and further into the compressed material 250. The compressed material 250 has expanded with addition of the fluids, pressing upwards against the lower wicking material 265 and the adjacent lower wall 275 of the cassette. This pressure has pushed the support material 225 upwards, correspondingly pushing upwards the first porous sheet 500 and the second porous sheet 510. The upper surface of the first porous sheet 500 has moved adjacent to the lower aperture 145 of the capillary valve 140, and the reagent fluid that was within the capillary valve 140 has moved into the adjacent first porous sheet 500. This results in the mixing of the reagent fluid with the existing mixture of the first fluid, the second fluid and the reagents that were present in the porous sheets as part of the progression of a multi-step biochemical assay within the assay device. The fluid and reagent mixture flows into the second porous sheet 505, creating a visual change that is detectable by a user through the visualization aperture 150 as the result of the biochemical assay.

Figure 15:
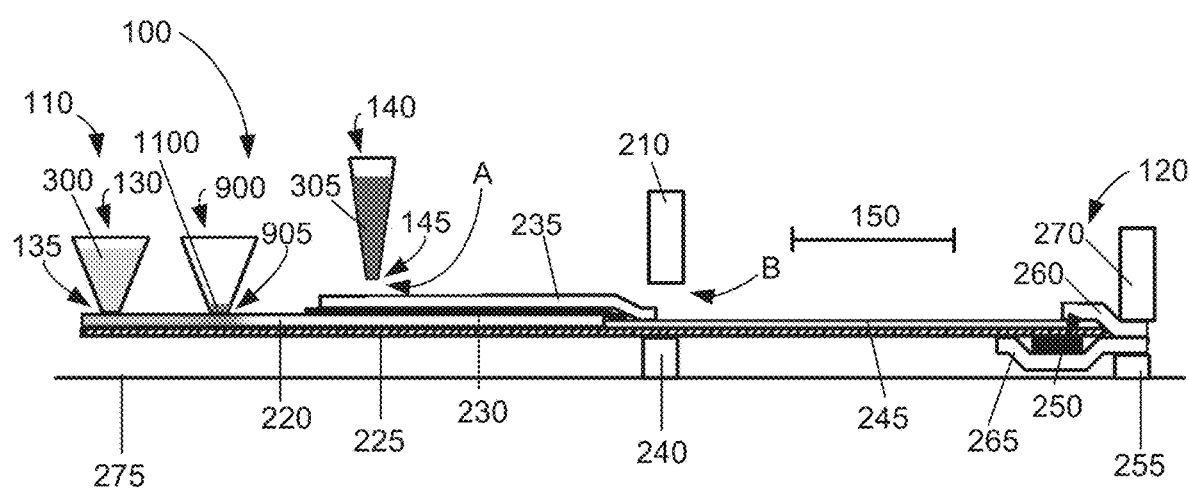
FIG. 15 is a cross section view of some features of a cassette and internal assay components.

FIG. 15 depicts features of an assay device 100 that includes a first porous sheet 220, a second porous sheet 245 and a third porous sheet 235 as well as both a first fluid well 130 and a second fluid well 900. Most of the cassette has been removed from the illustration of FIG. 15 for clarity, although the lower wall 275 of the cassette is depicted. A third porous sheet 235 partially overlays the second end of the first porous sheet 220 and the first end of the second porous sheet 245, including the junction between the first porous sheet 220 and the second porous sheet 245. A moisture barrier 230 is positioned between the lower surface of the third porous sheet 235 and the top surface of the first porous sheet 220, preventing direct fluid transfer between the first porous sheet 220 and the third porous sheet 235. The second end of the third porous sheet 245 extends beyond the second end of the moisture barrier 130, so that the second end of the third porous sheet contacts the second porous sheet 245 at a position near the first end of the second porous sheet 245. The capillary pressure of the first porous sheet is less than the capillary pressure of the second porous sheet, so fluid tends to flow from the first porous sheet into the second porous sheet. The capillary pressure of the third porous sheet is also lower than the capillary pressure of the second porous sheet, so fluid also tends to flow from the third porous sheet into the third porous sheet. The capillary pressure of the wicking material is lower than the capillary pressure of the third porous sheet, resulting in a tendency for fluid to move through the third porous sheet into the wicking material.

FIG. 15 is shown at a time point soon after a user has added a first fluid 300 to the first fluid well 130 and a second fluid 1100 to the second fluid well 900. The fluids 300, 1100 are moving through the respective lower apertures 135, 905 of the first fluid well 130 and the second fluid well 900 into the first porous sheet 220 as illustrated by the color gradient in the first porous sheet 220. The fluids mix within the first porous sheet, both with each other as well as with any dry reagents that were stored within the first porous sheet as required by the specific biochemical assay being implemented. A reagent fluid 305 has been added to the capillary valve 140 and is being held within the capillary valve 140. A gap A is positioned between the lower aperture 145 of the capillary valve 140 and the surface of the third porous sheet 235. A gap B is present between the top section of the mechanical pivot 210 and the second end of the third porous sheet 235 where it meets the top surface of the second porous sheet 245.

Figure 16:
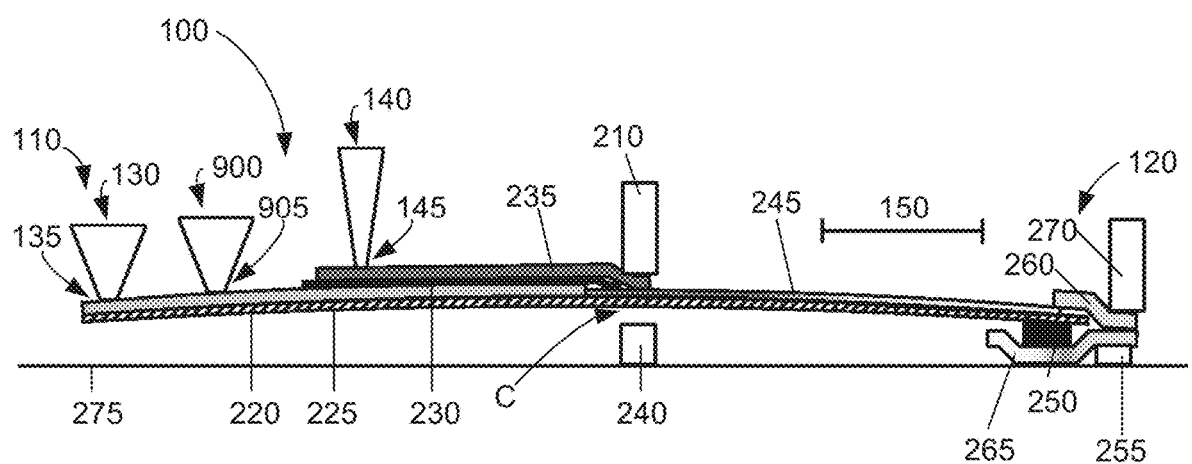
FIG. 16 is a cross section view of some features of a cassette and internal assay components.

FIG. 16 illustrates aspects of an assay device 100 during implementation of an assay. The assay device 100 shown in FIG. 16 is similar to the one depicted in FIG. 15, at a later stage in the assay. The fluids that were within the first fluid well 130 and the second fluid well 900 have moved through the respective lower apertures 135, 905 of the fluid wells 130, 900 into the first porous sheet 220. The fluids have moved along the first porous sheet 220 from the first end to the second end and into the second porous sheet 235. The fluids have further moved into the wicking material 260, 265 and still further into the compressed material 250. The compressed material 250 has expanded, causing upward movement of the support material 225 and consequently the porous sheets 220, 235, 245. This motion is limited by the distal end of the top portion of the mechanical pivot 210 against the top surface of the second end of the third porous sheet 235. The top surface of the third porous sheet 235 has moved to be adjacent with the lower aperture 145 of the capillary valve 140, and the reagent fluid that was within the capillary valve 140 has moved into the third porous sheet 235. The reagent fluid has then moved from the third porous sheet 235 into the second porous sheet 245 and mixed with the assay components within the second porous sheet 245, including components which were originally stored within one of the porous sheets 220, 235, 245 as well as components in the first fluid, the second fluid and the reagent fluid. A visual change in the second porous sheet 245 indicating the biochemical assay results can be seen by a user through the visualization aperture 150.

Example: Signal Amplification in a Lateral Flow Assay (LFA) Enabled by a Capillary Valve and Self-Actuating Elevator Valve Lateral flow assays (LFAs) are some of the most widely used diagnostic devices in resource-limited settings. However, they do not easily support chemistries that require multiple, time-delayed steps, which can greatly enhance assay performance. To address this shortfall, we developed a novel LFA design that combines liquid activation of an expanding material with a capillary valve to automate multi-step assays. The design is unique in that preserves the overall simplicity of the traditional LFA, as it enables minimal user intervention, is easy to use and interpret, and can be reel-to-reel manufactured at scale.

The lateral flow assay (LFA) is a diagnostic technology that has enabled point-of-care testing in a range of applications due to its low cost and non-instrumented format, which is operable by minimally trained personnel (E. B. Bahadir and M. K. Sezgintürk, "Lateral flow assays: Principles, designs and labels," *TrAC—Trends in Analytical Chemistry*, vol. 82. Elsevier B. V., pp. 286-306, September 2016, which is hereby incorporated by reference). The typical LFA comprises a series of porous materials that store dry reagents, drive flow, and bind/label a target of interest; a generic format that has remained mostly unchanged for decades. Improvements in specific aspects of the format have included new classes of binding elements, more sensitive labels, new materials with better reagent release or stability, and improved manufacturing methods (J. H. Soh, H. M. Chan, and J. Y. Ying, "Strategies for developing sensitive and specific nanoparticle-based lateral flow assays as point-of-care diagnostic device," *Nano Today*, vol. 30. Elsevier B. V., p. 100831, February 2020 which is hereby incorporated by reference). But while the LFA format enables wide distribution of immunoassays at the point of care, it limits support for more advanced chemistries and assays—such as enzymatic and redox chemistries, and nucleic acid amplification—which enhance diagnostic performance but increase operational complexity. Various enhanced LFAs have been demonstrated with the use of novel operational elements like hydrophobic barriers, dissolving elements, and expanding valves (E. Fu and C. Downs, "Progress in the development and integration of fluid flow control tools in paper microfluidics," *Lab on a Chip*, vol. 17, no. 4. Royal Society of Chemistry, pp. 614-628, February 2017 which is hereby incorporated by reference). However, to date such solutions are incompatible with existing scale manufacturing and therefore cannot leverage all advantages of the LFA format, especially with regards to cost and distribution.

To address these limitations, we developed a novel LFA that combines liquid activation of an expanding material, termed elevator valve, with a capillary valve to automate multi-step assays. Flow through the LFA into the expanding material causes elevation of the LFA position into contact with a capillary valve in the cassette. We first validated that this switching mechanism was reproducible, then we demonstrated that switch timing was tunable through the length and material choice of the LFA wicking pad material. The in-line design allows reel-to-reel scale manufacturing, and tuning of multi-step assays through changes in network geometry.

All devices used paper networks assembled with a second porous sheet fabricated from a nitrocellulose test membrane (Sartorius CN95), a first and third porous sheet utilizing two glass fiber sample/conjugate pads (Ahlstrom 8951) separated by double-sided tape (3M), and a wicking material on top of 60 mm adhesive backing cards (DCN); and compressed sponge (S&S Worldwide, Sponge Ums) and more wicking pad adhered by double-sided tape on bottom. Assembly shown in FIG. 10, with individual 4 mm strips cut from the larger assembly on a Kinematic Matrix guillotine cutter. Initial bench testing used pipette tips held above the network in an adjustable soldering jig. Cassette testing used a 3D-printed prototype cassette (VeroClear on Stratasys J750) designed in SolidWorks (Dassault Systémes). Our primary robustness metric was "time to activation," which was the time between the manual and the automated liquid addition steps.

Figure 17:
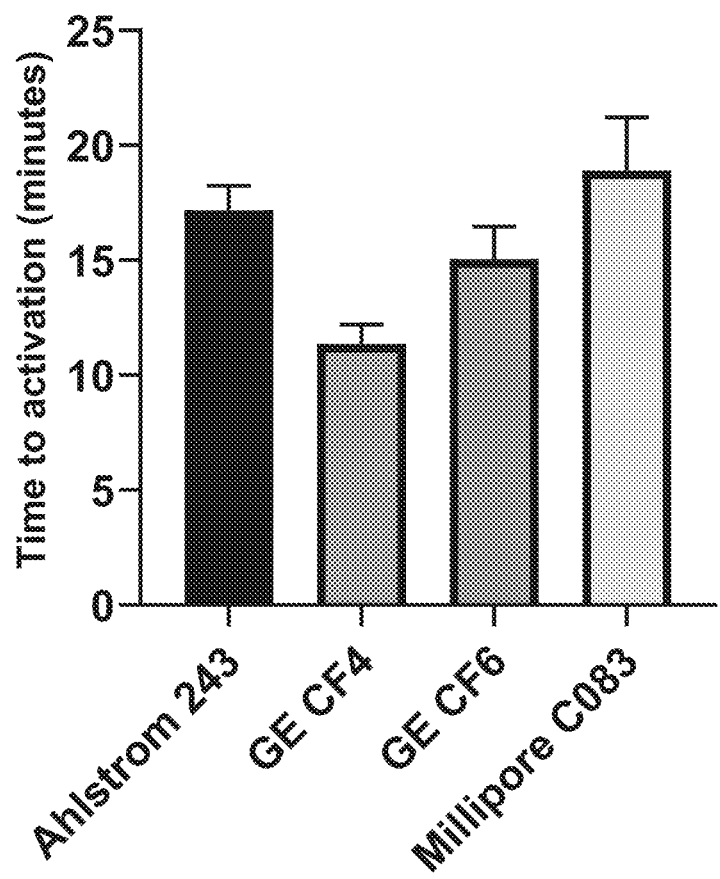
FIG. 17 is a graph of experimental data.
Figure 18:
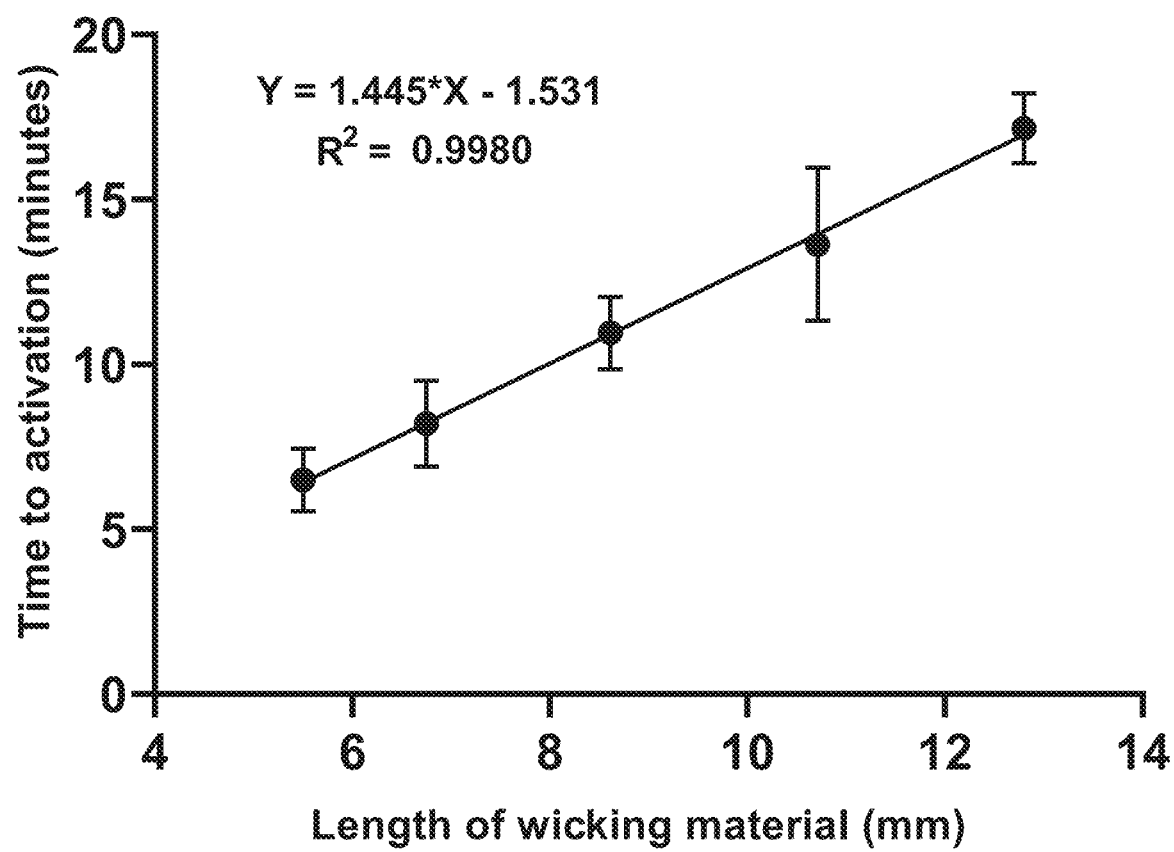
FIG. 18 is a graph of experimental data.

The goal for this work was to format a more sensitive assay in a paper network that could be operated and manufactured as easily as a traditional LFA. Building on research in paper and plastic microfluidics, we implemented the design shown in FIG. 15 and FIG. 16. This assay device switches the paper network into contact with a capillary valve in the cassette at a specific time. This switching delivers a second reagent set that, for example, amplifies the LFA signal. Simple geometric adjustments allow the designer to tune the time to activation. Experimental data from these tests are shown in FIG. 18 with time delay shown in minutes on the X axis and the length of the specific wicking material used shown in mm on the Y axis. A best fit line of the results is indicated. FIG. 18 illustrates, for example, that wicking materials 6 mm and 13 mm long activate the second step of the assay with delay times 10 minutes apart. Additionally, material choice of the wicking material changed the time delay period. Test results for different materials are illustrated in FIG. 17. FIG. 17 shows test data from wicking material composed of Ahlstrom 243, GE CF4, GE CF6 and Millipore CO83 in columns from right to left. The delays set through these material selection and size adjustments accommodate integration of a wide range of (at least) two-step assays with various timing requirements.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:
1. An assay device, comprising:
a cassette, including
an upper component with a fluid well, a capillary valve, a top section of a mechanical stop region, a top section of a mechanical compression region, and a visualization aperture,
a lower component with a bottom portion of the mechanical stop region and a bottom portion of the mechanical compression region; and
a set of assay components, including a porous sheet with a first end and a second end, a wicking material in contact with the second end of the porous sheet, and a compressed material of a size, shape and position to expand sufficiently when wet to move a top surface of the porous sheet adjacent to an aperture of the capillary valve.

2. The assay device of claim 1, wherein the upper component of the cassette and the lower component of the cassette mate together to form the cassette surrounding the set of assay components.

3. The assay device of claim 1, wherein the fluid well includes an aperture positioned adjacent to a top surface of the first end of the porous sheet within the cassette.

4. The assay device of claim 1, wherein the capillary valve includes an aperture positioned in alignment with a top surface of the porous sheet with a gap between the aperture and the top surface of the porous sheet within the cassette.

5. The assay device of claim 1, wherein the top section of the mechanical stop region includes an end positioned in alignment with a top surface of the porous sheet adjacent to the second end, with a gap between the end and the top surface of the porous sheet within the cassette.

6. The assay device of claim 1, wherein the top section of the mechanical compression region is positioned adjacent to a top surface of the wicking material and the bottom portion of the mechanical compression region is positioned adjacent to a bottom surface of the wicking material within the cassette.

7. The assay device of claim 1, wherein the wicking material is positioned adjacent to both a top surface and a bottom surface of the second end of the porous sheet and the mechanical compression region is positioned adjacent to the wicking material.

8. The assay device of claim 1, wherein the compressed material is positioned adjacent to the bottom surface of the porous sheet and in contact with the wicking material, and further comprising: a support material between the bottom surface of the porous sheet and the compressed material.

9. The assay device of claim 1, wherein the set of assay components are positioned in a parallel arrangement compatible with reel to reel immunoassay manufacturing techniques.

10. The assay device of claim 1, wherein the top component of the cassette further comprises: a second fluid well including an aperture positioned adjacent to a top surface of the first end of the porous sheet within the cassette.

11. An assay device, comprising:
a cassette, including
an upper component with a fluid well, a capillary valve, a top section of a mechanical stop region, a top section of a mechanical compression region, and a visualization aperture,
a lower component with a bottom portion of the mechanical stop region and a bottom portion of the mechanical compression region; and
a set of assay components, including a first porous sheet with a first end and a second end, a second porous sheet with a first end and a second end, wherein the second end of the first porous sheet is in contact with the first end of the second porous sheet, a wicking material in contact with the second end of the second porous sheet, and a compressed material of a size, shape and position to expand sufficiently when wet to move a top surface of the porous sheet adjacent to an aperture of the capillary valve.

12. The assay device of claim 11, wherein the upper component of the cassette and the lower component of the cassette mate together to form the cassette surrounding the set of assay components.

13. The assay device of claim 11, wherein the fluid well includes an aperture positioned adjacent to a top surface of the first end of the first porous sheet within the cassette.

14. The assay device of claim 11, wherein the capillary valve includes an aperture positioned in alignment with a top surface of either the first porous sheet or the second porous sheet with a gap between the aperture and the top surface of the first porous sheet or the second porous sheet within the cassette.

15. The assay device of claim 11, wherein the top section of the mechanical stop region includes an end positioned in alignment with a top surface of the first porous sheet adjacent to the second end, with a gap between the end and the top surface of the porous sheet within the cassette.

16. The assay device of claim 11, wherein the top section of the mechanical compression region is positioned adjacent to a top surface of the wicking material and the bottom portion of the mechanical compression region is positioned adjacent to a bottom surface of the wicking material within the cassette.

17. The assay device of claim 11, wherein the wicking material is positioned adjacent to both a top surface and a bottom surface of the second end of the second porous sheet and the mechanical compression region is positioned adjacent to the wicking material.

18. The assay device of claim 11, wherein the compressed material is positioned adjacent to the bottom surface of the second porous sheet and in contact with the wicking material, and further comprising a support material between the bottom surface of the second porous sheet and the compressed material.

19. The assay device of claim 11, wherein the set of assay components are positioned in a parallel arrangement compatible with reel to reel immunoassay manufacturing techniques.

20. The assay device of claim 11, wherein the top component of the cassette further comprises: a second fluid well including an aperture positioned adjacent to a top surface of the first end of the first porous sheet within the cassette.

21. An assay device, comprising:
a cassette, including
an upper component with a fluid well, a capillary valve, a top section of a mechanical stop region, a top section of a mechanical compression region, and a visualization aperture,
a lower component with a bottom portion of the mechanical stop region and a bottom portion of the mechanical compression region; and
a set of assay components, including a first porous sheet with a first end and a second end, a second porous sheet with a first end and a second end, a third porous sheet with a first end and a second end, wherein the second porous sheet overlays the second end of the first porous sheet and the first end of the third porous sheet, a wicking material in contact with the second end of the third porous sheet, and a compressed material of a size, shape and position to expand sufficiently when wet to move a top surface of the second porous sheet adjacent to an aperture of the capillary valve.

22. The assay device of claim 21, wherein the upper component of the cassette and the lower component of the cassette mate together to form the cassette surrounding the set of assay components.

23. The assay device of claim 21, wherein the fluid well includes an aperture positioned adjacent to a top surface of the first end of the first porous sheet within the cassette.

24. The assay device of claim 21, wherein the capillary valve includes an aperture positioned in alignment with a top surface of the second porous sheet with a gap between the aperture and the top surface of the second porous sheet within the cassette.

25. The assay device of claim 21, wherein the top section of the mechanical stop region includes an end positioned in alignment with a top surface of the second porous sheet adjacent to the second end, with a gap between the end and the top surface of the second porous sheet within the cassette.

26. The assay device of claim 21, wherein the top section of the mechanical compression region is positioned adjacent to a top surface of the wicking material and the bottom portion of the mechanical compression region is positioned adjacent to a bottom surface of the wicking material within the cassette.

27. The assay device of claim 21, further comprising: a moisture barrier positioned between the first porous sheet and the second porous sheet.

28. The assay device of claim 21, further comprising: a moisture barrier positioned between the first porous sheet, the third porous sheet and the second porous sheet.

29. The assay device of claim 21, wherein the wicking material is positioned adjacent to both a top surface and a bottom surface of the second end of the third porous sheet and the mechanical compression region is positioned adjacent to the wicking material.

30. The assay device of claim 21, wherein the compressed material is positioned adjacent to the bottom surface of the third porous material and in contact with the wicking material, and further comprising: a support material between the bottom surface of the third porous material and the compressed material.

31. The assay device of claim 21, wherein the set of assay components are positioned in a parallel arrangement compatible with reel to reel immunoassay manufacturing techniques.

32. The assay device of claim 21, wherein the top component of the cassette further comprises: a second fluid well including an aperture positioned adjacent to a top surface of the first end of the first porous sheet within the cassette.

* * * * *